(12) United States Patent
Cholevas

(10) Patent No.: US 12,734,038 B2
(45) Date of Patent: Sep. 15, 2026

(54) PATCH FOR COVERING A DEFECT IN THE ANNULUS FIBROSUS OF AN INTERVERTEBRAL DISC, AND IN PARTICULAR ALSO IN THE POSTERIOR LONGITUDINAL LIGAMENT, OF A SPINE

(71) Applicant: DISCOSEAL BV, Hoofdorp (NL)

(72) Inventor: Christos Cholevas, Trikala (GR)

(73) Assignee: DISCOSEAL BV, Hoofdorp (NL)

( * ) Notice: Subject to any disclaimer, the term of this patent is extended or adjusted under 35 U.S.C. 154(b) by 0 days.

(21) Appl. No.: 18/570,979

(22) PCT Filed: Jun. 14, 2022

(86) PCT No.: PCT/EP2022/066179
§ 371 (c)(1),
(2) Date: Dec. 15, 2023

(87) PCT Pub. No.: WO2022/263448
PCT Pub. Date: Dec. 22, 2022

(65) Prior Publication Data

US 2024/0277462 A1 Aug. 22, 2024

(30) Foreign Application Priority Data

Jun. 16, 2021 (EP) .................................... 21179868

(51) Int. Cl.
*A61F 2/44* (2006.01)

(52) U.S. Cl.
CPC ...... *A61F 2/442* (2013.01); *A61F 2002/4435* (2013.01)

(58) Field of Classification Search
CPC . A61B 17/80; A61B 17/8033; A61B 17/8047; A61B 17/8052; A61B 17/8057;
(Continued)

(56) References Cited

U.S. PATENT DOCUMENTS 5,380,328 A * 1/1995 Morgan .............. A61F 2/30965 606/70
7,824,433 B2 * 11/2010 Williams ........... A61B 17/8085 606/283
(Continued)

FOREIGN PATENT DOCUMENTS

AU 2012261709 B2 8/2015
CN 112210888 A 1/2021
(Continued)

OTHER PUBLICATIONS

European Search Report dated Jan. 24, 2022 from counterpart European Patent Application No. 21179868.1.
(Continued)

*Primary Examiner* — Eric S Gibson
(74) *Attorney, Agent, or Firm* — SHUTTLEWORTH & INGERSOLL, PLC; Timothy J. Klima

(57) ABSTRACT

The present invention refers to a patch for covering a defect in the annulus fibrosus of an intervertebral disc, and in particular also in the posterior longitudinal ligament, of a spine. A further aspect of the present invention refers to a surgical kit, including such a patch and at least one fastening element for fastening the patch body to the spine.

18 Claims, 4 Drawing Sheets

(58) Field of Classification Search
CPC ............ A61B 17/8061; A61B 17/8066; A61B 17/8071; A61B 17/8076; A61B 17/8085; A61F 2/44; A61F 2/442; A61F 2002/4435; A61F 2002/4495
See application file for complete search history.

(56) References Cited

U.S. PATENT DOCUMENTS 10,213,239 B2 * 2/2019 Koizumi ............... A61F 2/2803
2002/0123750 A1 * 9/2002 Eisermann ............ A61B 17/68 606/76
2006/0058881 A1 * 3/2006 Trieu ...................... A61F 2/442 623/17.16
2006/0264948 A1 * 11/2006 Williams ............... A61B 17/70 606/281
2007/0055375 A1 * 3/2007 Ferree ..................... A61F 2/442 623/17.11
2007/0067040 A1 * 3/2007 Ferree ..................... A61F 2/442 606/86 A
2007/0276494 A1 * 11/2007 Ferree ................ A61B 17/0401 623/17.11
2008/0147098 A1 * 6/2008 Trieu ................. A61B 17/8085 606/151
2009/0024147 A1 * 1/2009 Ralph ....................... A61F 2/36 606/151
2009/0138082 A1 * 5/2009 Reah ..................... A61F 2/4455 623/23.74
2010/0016889 A1 * 1/2010 Ferree ................... A61F 2/0063 606/228
2010/0057114 A1 * 3/2010 Butler .............. A61B 17/00234 606/151
2010/0087926 A1 * 4/2010 Butler ..................... A61F 2/442 606/300
2010/0256765 A1 * 10/2010 Butler ................... A61F 2/4611 606/151
2011/0224703 A1 9/2011 Mortarino
2012/0296440 A1 * 11/2012 Choux ................... A61B 17/68 623/23.52
2015/0148823 A1 5/2015 Mortarino et al.
2016/0183990 A1 * 6/2016 Koizumi ............ A61B 17/8085 606/285
2019/0274844 A1 9/2019 Seifert
2023/0114987 A1 * 4/2023 Mercuri ............. A61B 17/0401 623/17.16
2024/0277462 A1 * 8/2024 Cholevas ................ A61F 2/442

FOREIGN PATENT DOCUMENTS

EP 4104799 A1 * 12/2022 ........... A61F 2/0063
GR 2003119 Y 3/2018
WO 02067792 A2 9/2002
WO WO-2004093743 A1 * 11/2004 ......... A61B 17/8085
WO WO-2005041813 A2 * 5/2005 ............. A61F 2/441
WO WO-2005114120 A2 * 12/2005 ............. A61B 17/80
WO WO-2006119216 A1 * 11/2006 ............. A61B 17/70
WO 2008039530 A2 4/2008
WO WO-2008063169 A1 * 5/2008 ............. A61F 2/442
WO WO-2010028070 A1 * 3/2010 ....... A61B 17/00234
WO 2010040107 A1 4/2010
WO WO-2010114967 A1 * 10/2010 ............. A61F 2/441
WO WO-2011092417 A1 * 8/2011 ............. A61B 17/68
WO WO-2015030228 A1 * 3/2015 ......... A61B 17/8071
WO WO-2021111101 A1 * 6/2021 ............... A61F 2/02
WO WO-2022263448 A1 * 12/2022 ........... A61F 2/0063
WO WO-2023059887 A1 * 4/2023 ......... A61B 17/0401

OTHER PUBLICATIONS

International Search Report and Written Opinion dated Sep. 23, 2022 from counterpart International Patent Application No. PCT/EP2022/066179.

* cited by examiner

PATCH FOR COVERING A DEFECT IN THE ANNULUS FIBROSUS OF AN INTERVERTEBRAL DISC, AND IN PARTICULAR ALSO IN THE POSTERIOR LONGITUDINAL LIGAMENT, OF A SPINE

This application is the National Phase of International Application PCT/EP2022/066179 filed Jun. 14, 2022 which designated the U.S.

This application claims priority to European Patent Application No. 21179868.1 filed Jun. 16, 2021, which application is incorporated by reference herein.

The present invention refers to a patch for covering a defect in the annulus fibrosus of an intervertebral disc, and in particular also in the posterior longitudinal ligament, of a spine of a patient. The invention further refers to a surgical kit comprising such a patch and at least one fastening element for fastening the patch to a spine of a patient.

The spine of a person provides body structure and support, while allowing the person to move about freely and to bend with flexibility. The building blocks of the spine are the vertebrae. Between two adjacent vertebrae lies an intervertebral disc, which functions as a shock absorber, allows movement of the vertebrae and acts as a ligament to hold the vertebrae together. An intervertebral disc consists of an outer fibrous ring, the annulus fibrosus, which surrounds an inner gel-like centre, the nucleus pulposus. The posterior longitudinal ligament lies just posteriorly to the annulus fibrosus, covering the posterior surface of the spine vertebrae along with the associated discs.

An excessive strain or trauma to the spine may cause a crack, tear or rupture (defect) of the annulus fibrosus, through which a fragment of the nucleus pulposus can protrude into the spinal canal. This situation is called disc herniation and may result in a compression of the surrounding spinal nerves, what in turn causes pain and in many cases neurological complications to the person.

Two of the existing solutions for the treatment of a herniated disc are spinal fusion and artificial disc replacement. During spinal fusion, a direct connection between the vertebrae surrounding the herniated intervertebral disc is formed. Due the fixation of the vertebrae, the motion of the intervertebral disc is prevented and thus pain relief is achieved. However, this approach severely limits the motion of the affected part of the vertebral column. During artificial disc replacement, the herniated intervertebral disc is removed and replaced by a prosthetic implant, i.e. an artificial disc. However, disc replacement can only treat limited types of disc pathology.

Another solution for the treatment of disc herniation is microdiscectomy spine surgery, which aims to relieve pressure on a spinal nerve root by removing the intervertebral disc material that is responsible for it. The problem with this type of surgery is that, following the removal of the intervertebral disc material, a defect (through which the removal was performed) remains in the annulus fibrosus. This defect serves as a pathway for additional intervertebral disc material to protrude into the spinal canal, resulting in the recurrence of the herniation. Since thousands of patients each year require surgery to treat disc herniation and approximately five percent of these patients will suffer recurrent disc herniation condition, with substantial implications in terms of the cost of medical treatment and human suffering, an effective solution to this problem is needed.

GR 2003119 Y discloses a patch for preventing a recurrence of lumbar disc hernia. In particular, the patch is intended to securely cover the gap formed at the posterior longitudinal ligament and annulus fibrosus during microdiscectomy.

It is an object underlying the present invention to provide an improved patch for covering a defect in the annulus fibrosus of an intervertebral disc, and in particular also in the posterior longitudinal ligament, of a spine of a patient.

A patch for covering a defect in the annulus fibrosus of an intervertebral disc, and in particular also in the posterior longitudinal ligament, of a spine is disclosed. The patch comprises a patch body formed as a sheet.

The patch body (sheet) preferably has a first axis that lies on a main face of the patch body. Preferably, the patch body (sheet) has a second axis that lies on the main face of the patch body and is perpendicular to the first axis.

Due to the design of the patch body as a sheet, the patch body is advantageously made flexible and can easily be dealt with to cover a defect in the annulus fibrosus of an intervertebral disc, and in particular also in the posterior longitudinal ligament, of a spine.

In particular, the patch is used for covering a defect in the annulus fibrosus of an intervertebral disc, and in particular also in the posterior longitudinal ligament, of a spine after microdiscectomy spine surgery for treating disc herniation, in particular lumbar disc herniation.

The defect may preferably comprise a crack and/or a tear and/or a rupture in the annulus fibrosus of an intervertebral disc, and in particular also in the posterior longitudinal ligament. In particular, the patch is used to prevent material of the nucleus pulposus of the intervertebral disc from exiting through the defect. In particular, the defect may particularly comprise a crack and/or a tear and/or a rupture in the annulus fibrosus of an intervertebral disc after a microdiscectomy surgery for treating disc herniation, in particular lumbar disc herniation. As already mentioned above, in a microdiscectomy surgery, a fragment of the nucleus pulposus that may protrude into the spinal canal due to said defect is removed but the defect remains in the annulus fibrosus, wherein a gap is in particular left in the annulus fibrosus and in particular also the posterior longitudinal ligament. The patch particularly covers this gap.

The patch is advantageously used for completely covering said defect.

The patch is advantageously used for covering said defect in a posterior approach to the spine, in particular to the lumbar spine.

Further, the patch is advantageously used for causing sterile inflammation around it (the patch) so that scar tissue is formed by using the patch as a scaffold. This effect is specifically prominent when the patch body is formed as a mesh made of non-woven fibres, in particular when the mesh comprises or is made of tetrafluoroethylene fibres and/or expanded tetrafluoroethylene fibres. Due to its design, the patch is advantageously not used for fixation of the spine, in particular of the vertebrae to which the patch body is fastened/secured.

The patch body preferably has a tensile stiffness between 20000 N/m (20 N/mm) and 40000 N/m (40 N/mm), more preferably between 25000 N/m (25 N/mm) and 35000 N/m (35 N/mm), parallel to a first axis. The first axis lies on a main face of the patch body (sheet).

Due to the chosen tensile stiffness and the design of the patch body as a sheet, the patch is configured to cover the defect in the annulus fibrosus and thereby prevent the nucleus pulposus from exiting therethrough without compromising the kinematics of the spine, as the patch is able to elastically deform during movement of the spine. In other words, the proposed patch is flexible, wherein its flexibility is chosen such that the patch does not restrict spinal movement of the patient in its fixed state to the spine. Thus, in particular contrary to the already known solution presented above, the proposed patch does not alter the mechanics of the vertebrae, in particular it does not fix the vertebrae, to which it is attached. Thus, for example when a patient bends forward, i.e. when the patient flexes his/her spine, the patch can adapt to the movement of the spine and extend parallel to the first axis of the patch body. In other words, the patch/patch body is advantageously elastically deformable during movement of the spine, in particular in the direction of the first axis.

The patch body preferably has a tensile stiffness between 20000 N/m (20 N/mm) and 40000 N/m (40 N/mm), more preferably between 25000 N/m (25 N/mm) and 35000 N/m (35 N/mm), parallel to a second axis. The second axis lies on the main face of the patch body (sheet). The first axis and the second axis are vertical, i.e. perpendicular, to each other. Thus, the patch/patch body is advantageously elastically deformable during movement of the spine, in particular in the direction of the second axis.

Preferably, the first axis is more particularly substantially parallel to the longitudinal axis of the human body, when the patch is attached to the spine of the human body. In other words, the first axis preferably extends substantially parallel to a longitudinal axis of at least a part of the spine. As far as the second axis is concerned, the second axis is more particularly substantially parallel to the mediolateral axis of the human body, when the patch is attached to the spine of a human. The term "substantially" is used here to consider the fact that the spine of a person has a natural curvature.

Further, the first axis can preferably lie on a first symmetry plane of the patch body. Similarly, the second axis can preferably lie on a second symmetry plane of the patch body. In other words, the first axis may preferably a first symmetry axis of the main face of the patch body, while the second axis may preferably be a second symmetry axis of the main face of the patch body.

It is noted that the main face of a sheet is more particularly the face of the sheet that has the largest surface area.

Within the framework of the present invention, a sheet is in particular defined as an element with a thickness that is much smaller than any other dimension suitable for defining the sheet. For example, in the case of a sheet that has the shape of a parallelogram, the thickness of the sheet is much smaller than the other two dimensions, i.e. the length and the width, of the sheet. Here, the main face of the sheet is the face defined by the width and length of the sheet. In the case of a circular sheet, the thickness of the sheet is much smaller than the diameter of the circular sheet. Here, the main face has a circular shape.

The expression "much smaller" particularly means within the scope of the present invention "at least three times smaller", preferably "at least four times smaller", more preferably "at least five times smaller". Thus, the thickness of a sheet that has the shape of a parallelogram may for example be at least four times smaller than the length and at least four times smaller than the width of the sheet. In another example, the thickness of a sheet that has the shape of a parallelogram may be at least four times smaller than the width of the sheet and at least five times smaller than the length of the sheet.

Preferably, the patch body has a total tensile elongation (percent elongation) equal to or higher than 160% parallel to the first axis and/or parallel to the second axis. In other words, the total tensile elongation the patch body can undergo is equal or higher to 160% parallel to the first axis and/or parallel to the second axis.

Preferably, a tensile load of equal to or less than 150 N, more preferably a tensile load of equal to or less than 100 N, parallel to the first axis and/or parallel to the second axis is required for achieving a tensile elongation (percent elongation) of equal to or higher than 50% parallel to the first axis and/or parallel to the second axis, respectively. This configuration of the patch enables its elastic deformation under loads that are expected for a whole range of motion of the spine. Thus, the elastic deformation of the patch can match the displacement of the vertebrae, to which the patch may be attached, for the whole range of motion of the spine.

Within the scope of the present invention, the total tensile elongation of the patch body parallel to the direction of the first axis or the second axis is in particular the elongation percentage of the patch when one end of the patch body (sheet) is fixed and the other end of the patch body (sheet) is subjected to a tensile load parallel to the first or the second axis, respectively, and a failure of the patch occurs.

Preferably, the patch body has the same aforementioned mechanical properties on a plane parallel to a main face (of the patch body), in particular in the direction of every axis that lies on the main face.

Preferably, the patch body is made of a material that has a yield strength between $5\times10^6$ Pa (5 MPa) and $8\times10^6$ Pa (8 MPa). The yield strength or yield stress is the stress corresponding to the yield point at which a material begins to deform plastically.

Preferably, the patch body is formed as a mesh comprising non-woven fibres. In particular, the fibres are randomly distributed in the mesh. In other words, the patch body is preferably formed as a mesh made of non-woven fibres. An alternative formulation is that the patch body is preferably made of non-woven fibres. This means in other words that the patch body is preferably formed as a nonwoven fabric. The terms "nonwoven fabric" or "non-woven fibres" particularly denote/refer to a fabric that is neither woven nor knitted.

Preferably, the patch body is made as felt. Felt is in particular a non-woven fabric that is produced by matting, condensing and pressing fibres together.

Preferably, the mesh comprises/is made of polytetrafluoroethylene fibres and/or expanded polytetrafluoroethylene fibres. In other words, preferably, the non-woven fibres comprise polytetrafluoroethylene fibres and/or expanded polytetrafluoroethylene fibres or the non-woven fibres are polytetrafluoroethylene fibres and/or expanded polytetrafluoroethylene fibres.

The expression "a/the mesh is made of . . . " can advantageously be understood as "a/the mesh is completely made of . . . ". It is further understood that the term "mesh" in combination with the term "non-woven fibres" does in particular not mean/comprise a grid, a screen mesh, a lattice or a net.

Advantageously, the patch body is impermeable to the material of the nucleus pulposus of the intervertebral disc. Most preferably, the patch body is impermeable to fluids with viscosity up to 2000 mPa*s (milliPascal-second). This has the advantage that the material of the nucleus pulposus can be prevented from exiting the intervertebral disc in the whole range of motion of the spine.

The patch body preferably comprises at least one through opening for receiving a fastening element for fastening the patch to the spine. The at least one through opening is preferably a hole.

More preferably, the patch body comprises at least two through openings that are arranged in the direction of the first axis. Thus, the patch can be attached to the vertebrae on both sides of the intervertebral disc, i.e. the vertebrae, between which the affected intervertebral disc lies.

It is further advantageous if a reinforcing and/or stress distribution element is provided on the patch body around a boundary of the at least one through opening. Thus, on one hand, the reinforcing and/or stress distribution element acts as a protective means for the patch body around the at least one through opening, thereby reducing or eliminating the risk of tearing and/or abrasion of the patch body. On the other hand, said element may prevent a concentration of stresses around the at least one through opening by distributing stresses, e.g. caused by the fastening element, over a larger area of the patch body.

The reinforcing and/or distribution element is preferably made of metal or plastic.

Preferably, the reinforcing and/or stress distribution element is formed as an insert that is inserted in the at least one through opening. More particularly, the reinforcing and/or stress distribution element may be formed as a grommet. In particular, the grommet comprises a main body and at least one collar to be arranged on the patch body around the at least one through opening, in particularly around a boundary of the at least one through opening. The main body is inserted in the through opening. Preferably, the grommet comprises two collars, each of which is intended to be arranged on one of the main faces of the patch body.

Further, it is advantageous when the reinforcing and/or stress distribution element is fixedly connected to the patch body. The term "fixedly connected" means in particular that the reinforcing and/or stress distribution element cannot be removed from the patch body without being damaged and/or without damaging the patch body.

When the grommet comprises two collars, the collars are preferably pressed against the patch body so that the grommet is fixedly connected to the patch body.

It is advantageous if every through opening of the patch body is provided with a reinforcing and/or stress distribution element.

According to an advantageous embodiment, the patch body has the shape of a parallelogram, in particular a rectangular shape. This means that the main face(s) of the patch body is/are a parallelogram, in particular of rectangular shape. The cross-section of the patch body vertically, i.e. perpendicularly, to the first axis is advantageously of rectangular shape. The cross-section of the patch body vertically, i.e. perpendicularly, to the second axis is advantageously of rectangular shape.

Preferably, the patch body extends parallel to the first axis more than it extends parallel to the second axis.

The length of the patch body preferably lies in the range between 13 mm and 17 mm, in particular in the range between 14 mm and 16 mm.

The width of the patch body preferably lies in the range between 8 mm and 12 mm, in particular in the range between 9 mm and 11 mm.

The thickness of the patch body preferably lies in the range between 1 mm and 4 mm, more preferably between 2 mm and 3 mm.

According to an alternative advantageous embodiment of the present invention, the patch body may have a circular shape.

Preferably, the minimum distance between a boundary of the at least one through opening and a boundary of the patch body parallel to the first axis is at least 5%, preferably at least 10%, of the dimension of the patch body parallel to the first axis.

Similarly, the minimum distance between a boundary of the at least one through opening and a boundary of the patch body parallel to the second axis is preferably at least 5%, preferably at least 10%, of the dimension of the patch body parallel to the second axis.

It is understood that all the components of the patch are each made of a biocompatible material.

Further, the present invention refers to a surgical kit that comprises a patch as described above and at least one fastening element for fastening the patch body to the spine.

Further, the surgical kit may comprise at least one reinforcing and/or stress distribution element. The at least one reinforcing and/or stress distribution element can preferably be formed as the reinforcing and/or stress distribution element described above.

It is noted that all mechanical properties of or related to the patch can advantageously be measured by defining the load-displacement curve of the patch. For calculating the load displacement curve, a plurality of identical patches, in particular six identical patches, can be prepared. One end of the patch can be clamped in a vice attached to the base of a testing machine (Instron 8874; Instron, Norwood, MA, USA). The other end can be secured in a clamp attached to the functional column of the testing machine. Each patch can particularly be preloaded with 10 N for 30 seconds; then pulled at 1.25 mm/seconds to failure, with the data preferably captured at 100 Hz on a computer.

Further disclosed is the use of the previously described patch in a surgical method, in particular in a surgical method for covering a defect in the annulus fibrosus of an intervertebral disc, and in particular also in the posterior longitudinal ligament, of a spine of a patient. In particular, the method comprises the steps of providing a previously described patch and covering the defect in the annulus fibrosus of the intervertebral disc, and in particular also in the posterior longitudinal ligament, preferably by securing/fastening the patch to the vertrebrae, between which the intervertebral disc with the defect is arranged/lies.

The formulation "for covering a defect in the annulus fibrosus of an intervertebral disc, and in particular also in the posterior longitudinal ligament, of a spine" in particular means in the context of the present invention "for covering a defect in the annulus fibrosus of an intervertebral disc of a spine or for covering a defect in the annulus fibrosus of an intervertebral disc and the posterior longitudinal ligament of a spine".

The present invention also refers to a patch for covering a defect in the annulus fibrosus of an intervertebral disc, and in particular also in the posterior longitudinal ligament, of a spine, comprising a patch body that is formed as a sheet and as a mesh made of non-woven fibres, preferably the wherein mesh comprises polytetrafluoroethylene fibres and/or expanded polytetrafluoroethylene fibres. The patch is configured to cover the defect in the annulus fibrosus and thereby prevent the nucleus pulposus from exiting therethrough without compromising the kinematics of the spine, as the patch is able to elastically deform during movement of the spine.

These and further details, advantages and features of the present invention will be described based on embodiments of the invention and by taking reference to the accompanying FIGS. 1 to 9.

In the following, embodiments and the technical background of the present invention are presented in detail by taking reference to the accompanying FIGS. 1 to 9. Identical or equivalent elements and elements which act identically or equivalently are denoted with the same reference signs. Not in each case of their occurrence a detailed description of the elements and components is repeated.

Figure 1:
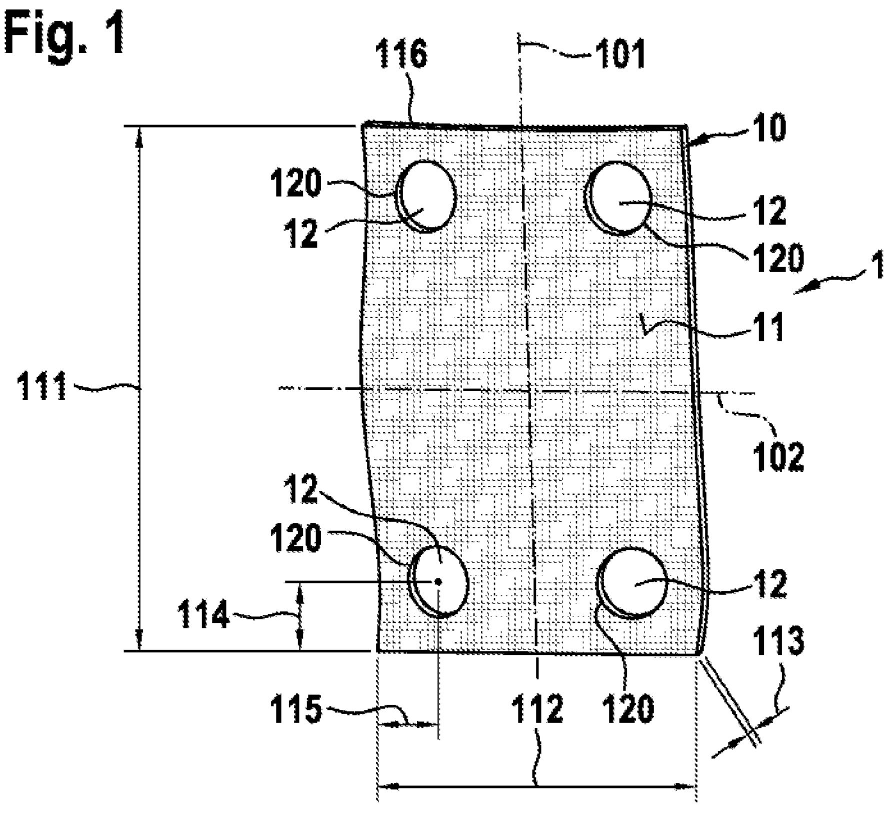
FIG. 1 is a schematic perspective view of a patch according to a first embodiment of the present invention.
Figure 3:
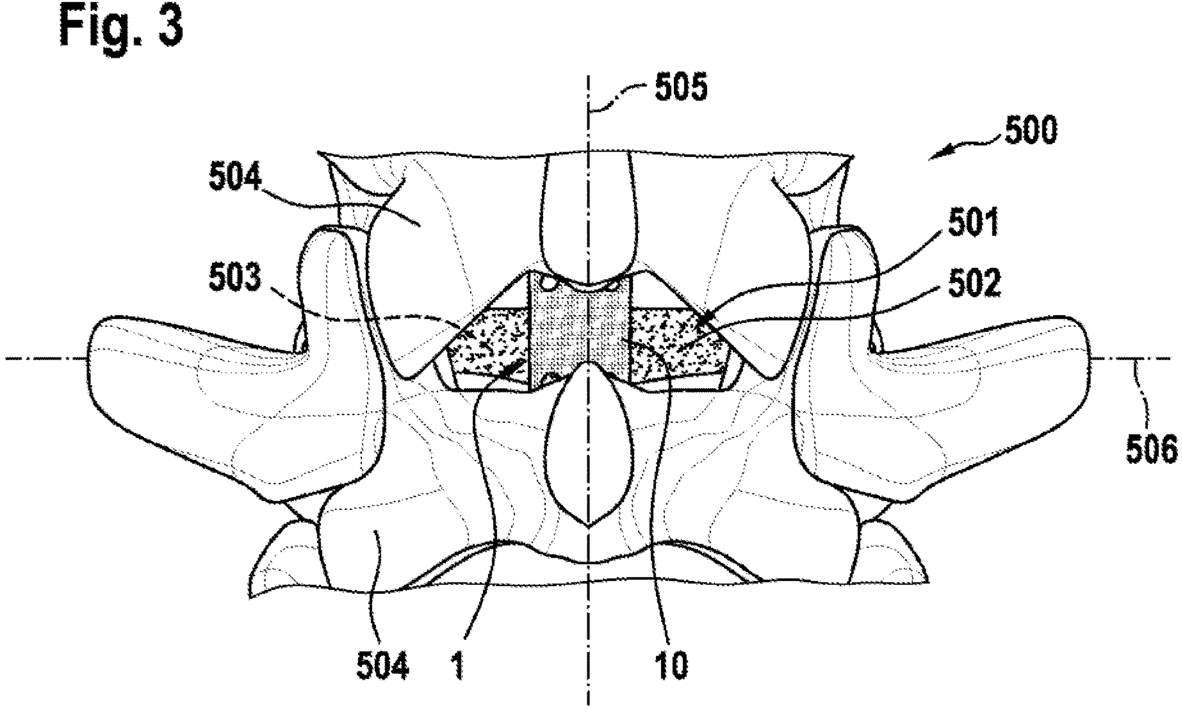
FIG. 3 is a schematic front view of a part of the spine of a person and the patch according to the first embodiment of the present invention fastened to the spine.
Figure 4:
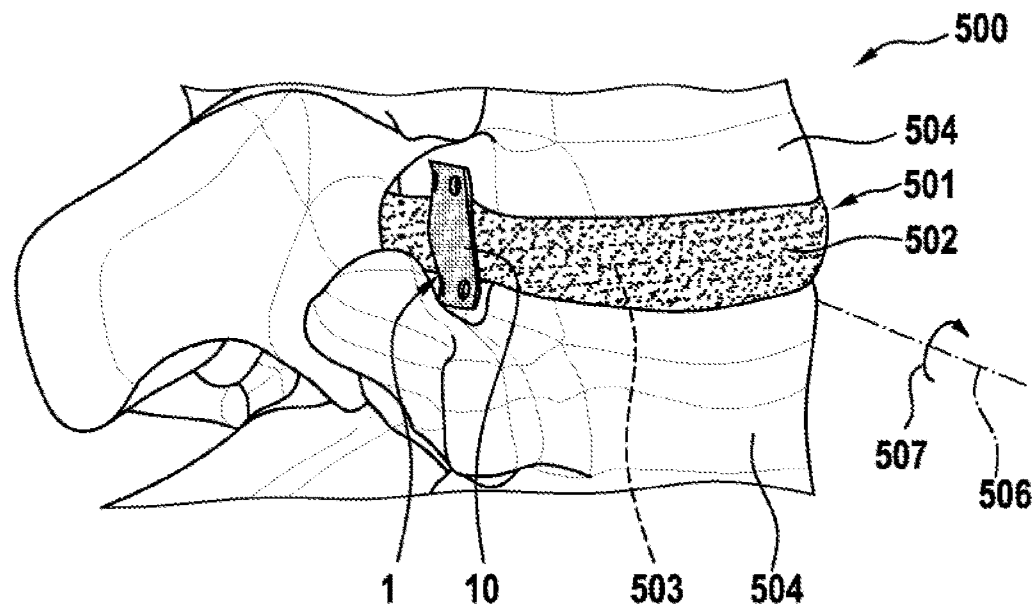
FIG. 4 is a schematic perspective view of a part of the spine of a person and the patch according to the first embodiment of the present invention fastened to the spine.

FIG. 1 shows a flexible patch 1 for covering a defect in the annulus fibrosus of an intervertebral disc, an in particular also of the posterior longitudinal ligament, of a spine of a patient according to the first embodiment of the present invention. A part of a spine 500 of a person represented by two vertebrae 504 and an intervertebral disc 501 is shown in FIGS. 3 and 4. For illustrative purposes, the posterior longitudinal ligament is not shown in the figures. When the intervertebral disc 501 has a defect in its annulus fibrosus 502, the patch 1 is intended to be attached to the spine 500 in order to cover said defect and prevent material of the nucleus pulposus 503 of the intervertebral disc 501 from exiting through the defect. This will be further explained with reference to FIGS. 3 and 4.

Referring back to FIG. 1, the patch 1 comprises a patch body 10 that is formed as a rectangular (flexible) sheet having a length 111, a width 112 and a thickness 113.

The fact that the patch body 10 is formed as a sheet means that its length 111 and width 112 are each much larger than its thickness 113. In particular, the length 111 and the width 112 of the patch body 10 may each be at least three times larger, preferably at least four times larger, and more preferably at least five times larger than the thickness 113 of the patch body 10. The length 111 of the patch body 10 extends in the direction of a first axis 101 of the patch body 10 and the width 112 in the direction of a second axis 102 of the patch body 10.

The first axis 101 and the second axis 102 are vertical to each other and lie on a main face 11 of the patch body 10. In particular, the first axis 101 and the second axis 102 lie on a first symmetry plane and a second symmetry plane of the patch body 10, respectively. In other words, the first axis 101 is a first symmetry axis and the second axis 102 a second symmetry axis of the main face 11 of the patch body 10.

It is noted that the length 111, width 112 and thickness 113 of the patch body 10 as well as the first axis 101 and the second axis 102 refer to the patch body 10 when it lies flat on a surface.

The patch body 10 has a tensile stiffness parallel to the first axis 101 that lies between $20\times10^3$ N/m and $40\times10^3$ N/m, in particular between $25\times10^3$ N/m and $35\times10^3$ N/m. Further, the patch body 10 has a tensile stiffness parallel to the second axis 102 that lies between $20\times10^3$ N/m and $40\times10^3$ N/m, in particular between $25\times10^3$ N/m and $35\times10^3$ N/m. Due to this configuration, the patch 1 is able to deform by the forces being exerted on the vertebrae 504 and consequently also to the body patch 10 being attached to the vertebrae 504 during movement of the spine 500. Thereby, the patch 1 does not limit but rather follows a movement of the vertebrae 504 relative to each other.

Preferably, the patch body 10 has a total tensile elongation equal to or higher than 160% parallel to the first axis 101 and parallel to the second axis 102. The patch body 10 is further configured such that a tensile load of equal to or less than 150 N, preferably a tensile load of equal to or less than 100 N, is required for achieving a tensile elongation equal to or higher than 50% in the corresponding direction.

Further, the patch body 10 is formed as a mesh made of non-woven fibres. The mesh comprises polytetrafluoroethylene fibres and/or expanded polytetrafluoroethylene fibres. In addition, the patch body 10 is impermeable to the material of the nucleus pulposus 503 of the intervertebral disc 501.

In addition, the polytetrafluoroethylene and/or expanded polytetrafluoroethylene fibres have a yield strength between $5\times10^6$ Pa and $8\times10^6$ Pa. Thus, they can withstand the forces that are exerted on the patch 1 during movement of the spine 500.

It can further be seen from FIG. 1 that the patch body 10 comprises a plurality of through openings 12, in particular through holes, for receiving a corresponding number of fastening elements. More specifically, four through openings 12 are provided in the patch body 10 of the present embodiment, which are pairwise arranged in the direction of the first axis 101.

The minimum distance 114 between a boundary 120 of each of the through openings 12 and a boundary 116 of the patch body 10 parallel to the first axis 101 is at least 5%, preferably at least 10%, of the length 111 of the patch body 10.

Similarly, the minimum distance 115 between the boundary 120 of each of the through openings 12 and the boundary 116 of the patch body 10 parallel to the second axis 102 is at least 5%, preferably at least 10%, of the width 112 of the patch body 10.

Due to the described arrangement of the through openings 12 relative to the boundary 116 of the patch body 10, the risk of a tear of the patch body 10 around the through openings 12 can be reduced.

Figure 2:
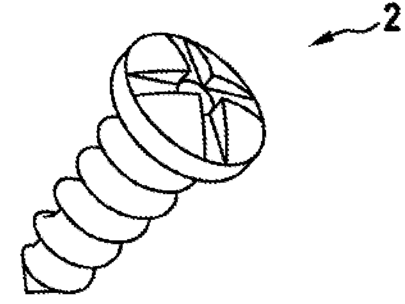
FIG. 2 is a schematic perspective view of a fastening element for fastening the patch to the spine of a person.

FIG. 2 shows a screw that can be used as each of the fastening elements 2 for fastening the patch body 10 to the spine 500.

The patch 1 and the plurality of the fastening elements 2 form a surgical kit.

In FIGS. 3 and 4, the patch 1 is shown in a state that it is affixed to the spine 500 for covering the defect in the annulus fibrosus 502 of the intervertebral disc 501.

More specifically, the patch 1 is fastened to the vertebrae 504, between which the intervertebral disc 501 having the defect lies. For a better overview, the fastening elements 2, via which the fixation of the patch 1 to the vertebrae 504 is realised, are omitted from FIGS. 3 and 4.

It can particularly be understood from FIG. 4 that, in its affixed state to the spine 500, the patch 1 has taken the shape of the intervertebral disc 501 and the vertebrae 504 in its overlapping areas with the intervertebral disc 501 and the vertebrae 504, respectively. Thus, due to its flexibility, the patch 1 is able to effectively seal the defect in the annulus fibrosus 502 of the intervertebral disc 501.

It can be further derived from FIG. 3 that the first axis 101 of the patch body 10 is substantially parallel to the longitudinal axis 505 of the person's body, while the second axis 102 is substantially parallel to the mediolateral axis 506 of the person's body.

Figure 5:
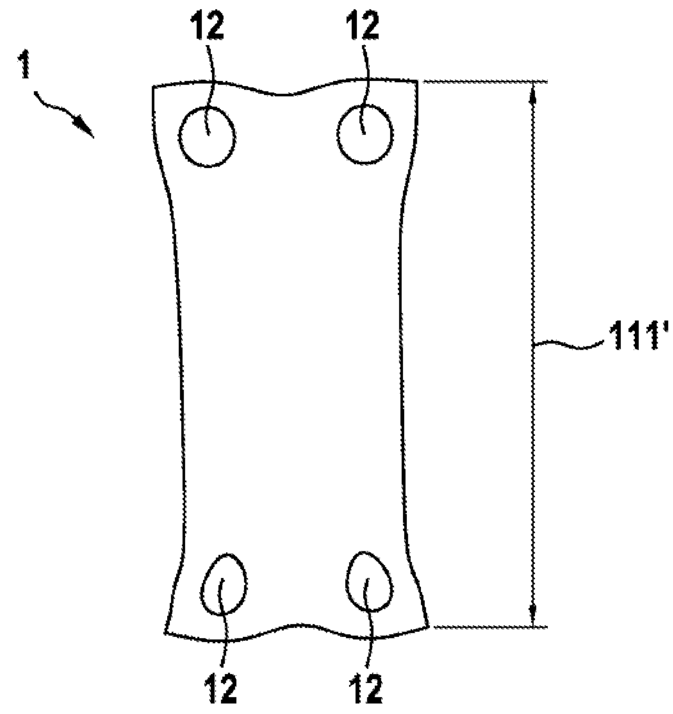
FIG. 5 is a schematic front view of an example of a deformed patch according to the first embodiment of the present invention after having been subjected to a tensile load.
Figure 6:
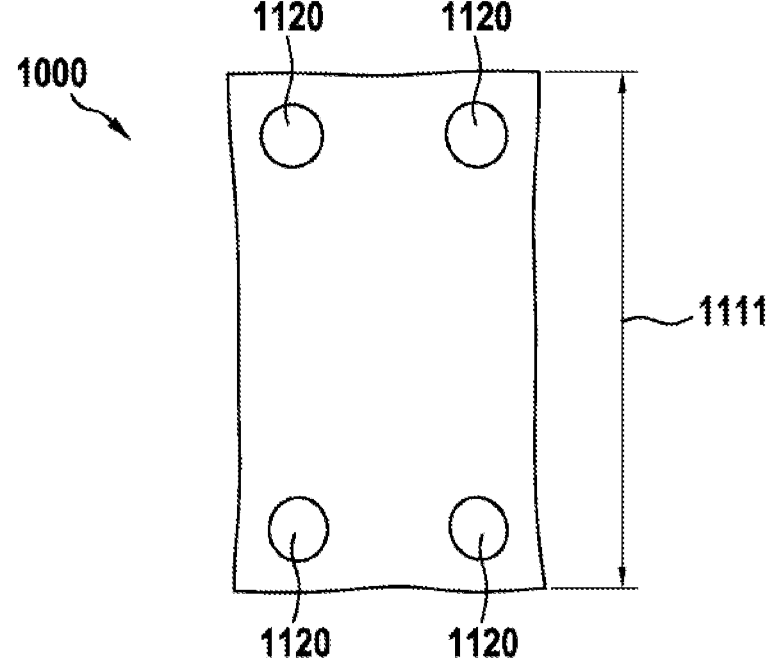
FIG. 6 is a schematic front view of a deformed patch not subject to the present invention after it has been subjected to the same tensile load as the patch of FIG. 5.

To highlight the advantages of the patch 1 of the present invention, the result of a simulation (finite element analysis) of an exemplary embodiment of a patch 1 of the present invention being subjected to a tensile force of 50 N parallel to the first axis 101, as shown in FIG. 5, is compared to the result of a simulation (finite element analysis) of an example of another patch 1000 (not according to the present invention) being subjected to the same tensile force, as shown in FIG. 6. It is noted that FIGS. 5 and 6 show the deformed patches 1, 1000 after they have each been subjected to the aforementioned tensile load parallel to the first axis 101.

Both patches 1, 1000 have the same initial dimensions prior to loading. In particular, the patches 1, 1000 have a length of 15 mm, a width of 10 mm and a thickness of 2.5 mm. Further, all through openings 12 of the patch 1 are formed as through holes with a circular cross-section with a diameter of 2 mm, wherein a distance between the centre of the circular cross-section of the through holes parallel to the first axis 101 is 11 mm and a distance between the centre of the circular cross-section of the through holes parallel to the second axis 102 is 6 mm. The patch 1000 comprises through openings 12 that are in terms of their size, shape and positional arrangement on the patch body 1000 identical to the through openings 12 of the patch 1. On the other hand, the patch 1 according to the exemplary embodiment of the present invention has a tensile stiffness of $30\times10^3$ N/m parallel to the first axis 101 and the second axis 102 and is formed as a mesh comprising polytetrafluoroethylene and/or expanded polytetrafluoroethylene fibres, whereas the patch 1000 has a tensile stiffness of $700\times10^3$ N/m in the corresponding directions and is made of PTFE (solid material not made of fibres).

The length of the deformed patch 1 of the present invention is denoted by the reference sign 111' in FIG. 5, while the length of the example of the deformed patch 1000 is denoted by the reference sign 1111 in FIG. 6.

When comparing FIGS. 5 and 6, it becomes apparent that the length 111' of the deformed patch 1 according to the exemplary embodiment of the present invention is greater than the length 1111 of the patch 1000. In other words, the patch 1 according to the exemplary embodiment of the present invention has experienced a greater tensile deformation parallel to the first axis 101 than the tensile deformation that the patch 1000 according to the example not being subject to the present invention has experienced in the corresponding direction.

In particular, the tensile deformation of the patch 1 at the middle of the patch body 10 in a direction parallel to the first axis 101 according to the exemplary embodiment of the present invention is 1.7 mm, whereas the corresponding tensile deformation of the patch 1000 is 0.068 mm.

Thus, the patch 1 according to the exemplary embodiment of the present invention is able to sufficiently deform in an elastic manner during the movement of the spine 500, thereby matching the displacement of the vertebrae 504 relative to each other, e.g. during a bending movement of the person as denoted by arrow 507 in FIG. 4. Further, the force needed for achieving said deformation lies within the range of the forces exerted on the vertebrae 504 during the movement of the spine 500. On the contrary, the patch 1000 is so stiff that it would negatively affect the mobility of the spine 500 and more specifically of the vertebrae 504.

Figure 7:
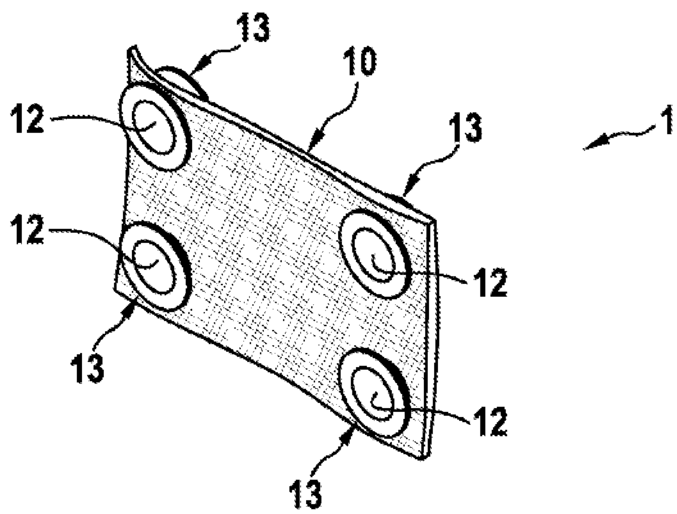
FIG. 7 is a schematic perspective view of a patch according to a second embodiment of the present invention.
Figure 8:
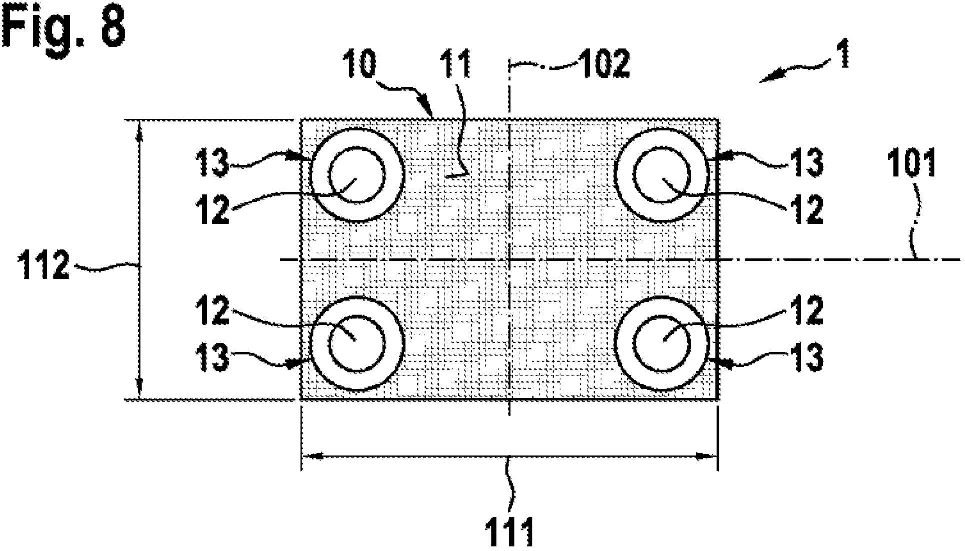
FIG. 8 is a schematic front view of the patch according to the second embodiment of the present invention.
Figure 9:
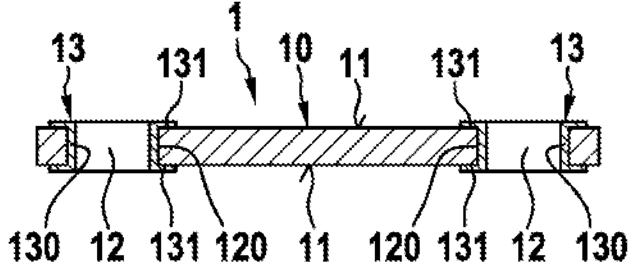
FIG. 9 is a schematic cross-sectional view of the patch according to the second embodiment of the present invention.

FIGS. 7 to 9 refer to a patch 1 according to a second embodiment of the present invention.

The patch 1 according to the second embodiment differs from the patch 1 according to the first embodiment in that the patch 1 according to the second embodiment comprises a plurality, in particular four, reinforcing and stress distribution elements 13.

Each reinforcing and stress distribution element 13 is provided on the patch body 10 around the boundary 120 of a corresponding through opening 12.

Further, each of the reinforcing and stress distribution elements 13 is formed as an insert that is inserted in a corresponding through opening 12. In particular, all reinforcing and stress distribution elements 13 are formed as grommets that are made of plastic or metal and each have a main grommet body 130 and two collars 131 integrally formed with the main grommet body 130. Each collar 131 is arranged on a main face 11 of the patch body 10, while the main grommet body 130 is inserted in the through opening 12.

The reinforcing and/or stress distribution elements 13 can in particular be fixedly connected to the patch body 10.

The reinforcing and stress distribution elements 13 provide protection to the patch body 10 around the through openings 12 and are configured to prevent or minimize stress concentrations around the through openings 12 by distributing stresses over a larger area of the patch body 10.

The depicted and described features and further properties of the invention's embodiments can arbitrarily be isolated and recombined without leaving the gist of the present invention.

Though the patch 1 according to the first and second embodiments has been described and is primarily intended as a solution for covering a defect in the annulus fibrosus of an intervertebral disc of a spine of a human, it is possible that the patch 1 can be used in animals, in particular primates, as well.

In addition to the foregoing description of the present invention, for an additional disclosure explicit reference is taken to graphic representation of FIGS. 1 to 9.

LIST OF REFERENCE SIGNS

1 patch
2 fastening element
10 patch body
11 main face
12 through opening
13 reinforcing and/or stress distribution element
101 first axis
102 second axis
111 length
111' length
112 width
113 thickness
114 distance
115 distance
116 boundary
120 boundary
130 main grommet body
131 collar
500 spine
501 intervertebral disc
502 annulus fibrosus

503 nucleus pulposus
504 vertebra
505 longitudinal axis
506 mediolateral axis
507 arrow
1000 patch
1111 length
1120 through opening

The invention claimed is:

1. A patch for covering a defect in an annulus fibrosus of an intervertebral disc of a spine, comprising:

a patch body that is formed as a sheet and has a tensile stiffness between $20\times10^3$ N/m and $40\times10^3$ N/m, parallel to a first axis, wherein the first axis lies on a main face of the patch body, wherein the patch body also has a second axis, wherein the second axis lies on the main face of the patch body and is vertical to the first axis.

2. The patch according to claim 1, wherein the patch body has a total elongation equal to or higher than 160% parallel to the first axis and/or the second axis.

3. The patch according to claim 1, wherein the patch body is configured such that, for achieving a tensile elongation equal to or higher than 50% parallel to the first axis, a tensile load of equal to or less than 150N is required parallel to the first axis, and/or wherein the patch body is configured such that, for achieving a tensile elongation equal to or higher than 50% parallel to the second axis, a tensile load of equal to or less than 150N is required parallel to the second axis.

4. The patch according to claim 1, wherein the patch body is made of a material that has a yield strength between $5\times10^6$ Pa and $8\times10^6$ Pa.

5. The patch according to claim 1, wherein the patch body comprises at least one through opening for receiving a fastening element for fastening the patch to the spine.

6. The patch according to claim 5, wherein a reinforcing and/or stress distribution element is provided on the patch body around a boundary of the at least one through opening, wherein the reinforcing and/or stress distribution element is made of metal or plastic.

7. The patch according to claim 6, wherein the reinforcing and/or stress distribution element is formed as an insert that is inserted in the at least one through opening.

8. The patch according to claim 6, wherein the reinforcing and/or stress distribution element is fixedly connected to the patch body.

9. The patch according to claim 5, wherein a minimum distance between a boundary of the at least one through opening and a boundary of the patch body is at least 5% of a dimension of the patch body parallel to the first axis and/or the second axis.

10. The patch according to claim 5, wherein a minimum distance between a boundary of the at least one through opening and a boundary of the patch body is at least 10% of a dimension of the patch body parallel to the first axis and/or the second axis.

11. The patch according to claim 1, wherein the patch body has a rectangular shape and/or wherein the patch body extends parallel to the first axis more than it extends parallel to the second axis.

12. The patch according to claim 1, wherein the patch body is formed as a mesh made of non-woven fibers.

13. The patch according to claim 12, wherein the mesh comprises/is made of polytetrafluoroethylene fibers and/or expanded polytetrafluoroethylene fibers.

14. A surgical kit, comprising the patch according to claim 1 and at least one fastening element for fastening the patch body to the spine.

15. The patch according to claim 1, wherein the patch is also configured for covering a defect in a posterior longitudinal ligament of the spine.

16. The patch according to claim 1, wherein:

the tensile stiffness is between $25\times10^3$ N/m and $35\times10^3$ N/m parallel to the first axis, and wherein the tensile stiffness is between $25\times10^3$ N/m and $35\times10^3$ N/m parallel to the second axis.

17. The patch according to claim 1, wherein the patch body is configured such that, for achieving a tensile elongation equal to or higher than 50% parallel to the first axis, a tensile load of equal to or less than 100 N, is required parallel to the first axis, and/or wherein the patch body is configured such that, for achieving a tensile elongation equal to or higher than 50% parallel to the second axis, a tensile load of equal to or less than 100 N, is required parallel to the second axis.

18. The patch according to claim 1, wherein the patch body has a tensile stiffness between $20\times10^3$ N/m and $40\times10^3$ N/m, parallel to a second axis, wherein the second axis lies on the main face of the patch body and is vertical to the first axis.

* * * * *